(12) United States Patent
Yabusaki

(10) Patent No.: US 6,594,001 B1
(45) Date of Patent: Jul. 15, 2003

(54) POLLEN GRAIN-COUNTING METHOD AND POLLEN GRAIN COUNTER

(75) Inventor: Katsumi Yabusaki, Tsukuba (JP)

(73) Assignee: Kowa Company, Ltd., Aichi (JP)

( * ) Notice: Subject to any disclaimer, the term of this patent is extended or adjusted under 35 U.S.C. 154(b) by 0 days.

(21) Appl. No.: 09/744,797
(22) PCT Filed: Jul. 27, 1999
(86) PCT No.: PCT/JP99/04013
§ 371 (c)(1),
(2), (4) Date: Jan. 26, 2001
(87) PCT Pub. No.: WO00/06994
PCT Pub. Date: Feb. 10, 2000

(30) Foreign Application Priority Data

Jul. 27, 1998 (JP) .......................................... 10-211639

(51) Int. Cl.$^7$ ............................................... G01N 21/00
(52) U.S. Cl. .......................... 356/73; 73/28.05; 73/28.06
(58) Field of Search .................. 356/73, 336, 417, 356/339, 338; 73/862.21, 862.22, 28.05, 28.06; 377/10

(56) References Cited

U.S. PATENT DOCUMENTS

| | | | | |
|---|---|---|---|---|
| 4,301,002 A | * | 11/1981 | Loo | 209/143 |
| 4,689,052 A | * | 8/1987 | Ogren et al. | 55/338 |
| 4,986,657 A | | 1/1991 | Ohe | |
| 5,275,787 A | * | 1/1994 | Yuguchi et al. | 209/579 |
| 5,367,474 A | | 11/1994 | Auer et al. | |
| 5,701,012 A | | 12/1997 | Ho | |
| 5,967,332 A | * | 10/1999 | Willeke | 209/132 |
| 6,133,995 A | * | 10/2000 | Kubota | 356/337 |
| 6,386,015 B1 | * | 5/2002 | Rader et al. | 73/23.33 |

FOREIGN PATENT DOCUMENTS

| | | | |
|---|---|---|---|
| JP | 7-5317671 | * | 12/1993 |
| JP | 7-6-34518 | * | 2/1994 |
| JP | 7-83830 | * | 3/1995 |
| JP | 7-10-19755 | * | 1/1998 |
| JP | 10-318908 A | * | 12/1998 |
| JP | 11-337469 A1 | * | 12/1999 |
| WO | WO 98/41876 | | 9/1998 |

OTHER PUBLICATIONS

Pinnick, Ronald G., et al., "Fluorescence Particle Counter for Detecting Airborne Bacteria and other Biological Particles", *Aerosol Science and Technology*, vol. 23, pp. 653–664 (1995).

* cited by examiner

Primary Examiner—Diane I. Lee
(74) Attorney, Agent, or Firm—Kilpatrick Stockton LLP (57) ABSTRACT

Provided is a method and apparatus which enable only pollen existing in the atmosphere to be automatically quantified. According to the method and apparatus, particles other than those substantially smaller than pollen grains, contained in a given amount of atmosphere, are separated; the separated particles are caused to flow through a flow cell in such a state that self-fluorescence from each of the particles can be measured; self-fluorescence from each of the particles passing through the flow cell is measured; and the number of particles is counted based on a measured value.

10 Claims, 4 Drawing Sheets

POLLEN GRAIN-COUNTING METHOD AND POLLEN GRAIN COUNTER

TECHNICAL FIELD

The present invention relates to a method and apparatus for counting pollen grains floating in the atmosphere.

BACKGROUND ART

As a method of counting pollen grains in the atmosphere, a real-time measuring method based on grain-diameter measurement utilizing light scattering has been developed, and a measuring apparatus based on this method is attracting attention.

This method, however, identifies pollen only through the grain size and therefore there is the problem of not necessarily quantifying pollen.

DISCLOSURE OF THE INVENTION

An object of the present invention is to provide a method and apparatus which enable only pollen existing in the atmosphere to be automatically quantified.

The present inventors have achieved the present invention by focusing on the characteristics of pollen and its detection by self-fluorescence, resulting to the solution of the above-described problem.

In a first aspect of the present invention, it is provided a pollen grain-counting method comprising separating particles other than those substantially smaller than pollen grains, contained in a given amount of atmosphere, causing the separated particles to flow through a flow cell in such a state that self-fluorescence from each of the particles can be measured, measuring self-fluorescence from each of the particles passing through the flow cell, and counting the number of particles based on a measured value (also referred to as the method of the present invention, hereinafter).

In the method of the present invention, separating is preferably performed by a virtual impactor. Also, scattered light is preferably measured together with the self-fluorescence, and the scattered light to be measured preferably includes forward scattered light and side scattered light. Also, the number of particles is preferably counted based on a ratio of a blue component and a red component of measured self-fluorescence.

In a second aspect of the invention, it is provided a pollen-counting apparatus comprising a separating means of separating particles other than those substantially smaller than pollen grains, contained in a given amount of atmosphere, a fluidizing means of causing the separated particles to flow through a flow cell in such a state that self-fluorescence from each of particles can be measured, a measuring means of measuring self-fluorescence from each of the particles passing through the flow cell, a counting means of counting the number of particles based on a measured value, and an outputting means of outputting a count result (also referred to as the apparatus of the present invention, hereinafter).

In the apparatus of the present invention, the separating means is preferably a virtual impactor. Also, the measuring means preferably comprises means of measuring scattered light, and more preferably a means of measuring forward scattered light and a means of measuring side scattered light. It is also preferred that the measuring means comprises a means of measuring a blue component and a red component of the self-fluorescence.

BEST MODE FOR CARRYING OUT THE INVENTION

The method of the present invention and the apparatus of the present invention will be described one by one.

<1> Method of the Present Invention

The method of the present invention is characterized by separating particles other than those substantially smaller than pollen grains, contained in a given amount of atmosphere, causing the separated particles to flow through a flow cell in such a state that self-fluorescence from each of the particles can be measured, measuring self-fluorescence from each of the particles passing through the flow cell, and counting the number of particles based on a measured value.

Figure 1:
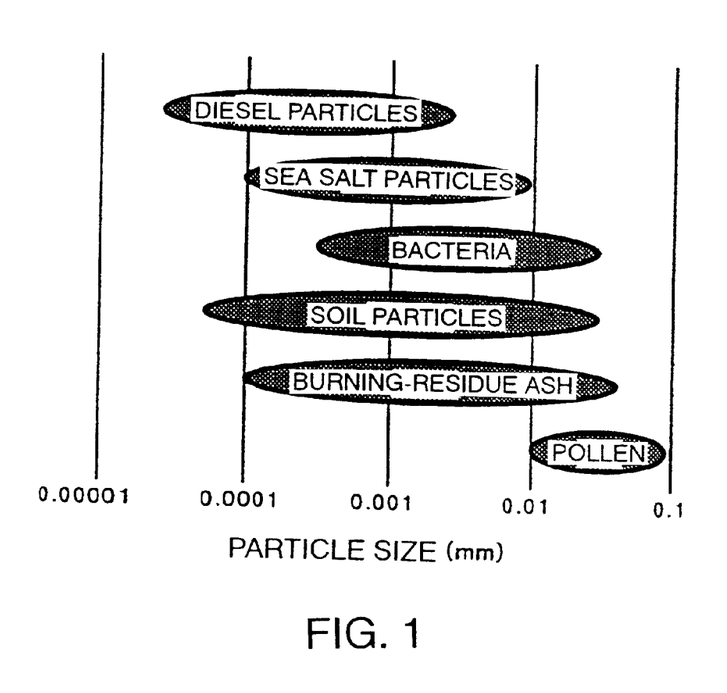
FIG. 1 is a diagram showing particles in the atmosphere and the size of the particles.

Particulates floating in the atmosphere, i.e., air, include diesel particles, burning-residue ash, soil particles, sea salt particles, bacteria, pollen, etc. Such particles vary in size through a certain range. However, pollen is one of the largest ones in these kinds of particles (FIG. 1). In the method of the present invention, therefore, particles other than those substantially smaller than pollen grains are separated. "Particles substantially smaller than pollen grains" denote such particles that, if they are removed, the proportion of particles other than pollen in the particles flowing through the flow cell is reduced sufficiently enough to facilitate measurement of self-fluorescence from each of the particles. For example, such particles are those having a particle size smaller than 6 $\mu$m.

Any method may be used for separating particles other than those substantially smaller than pollen grains. However, a method using a virtual impactor is preferred.

A virtual impactor separates particles according to the particle size, based on the phenomenon in which when a flow of air containing particles of various sizes changes, larger particles move straight because of their inertia but smaller particles move along the flow. In the present invention, a virtual impactor of well-known construction can be used.

Figure 2:
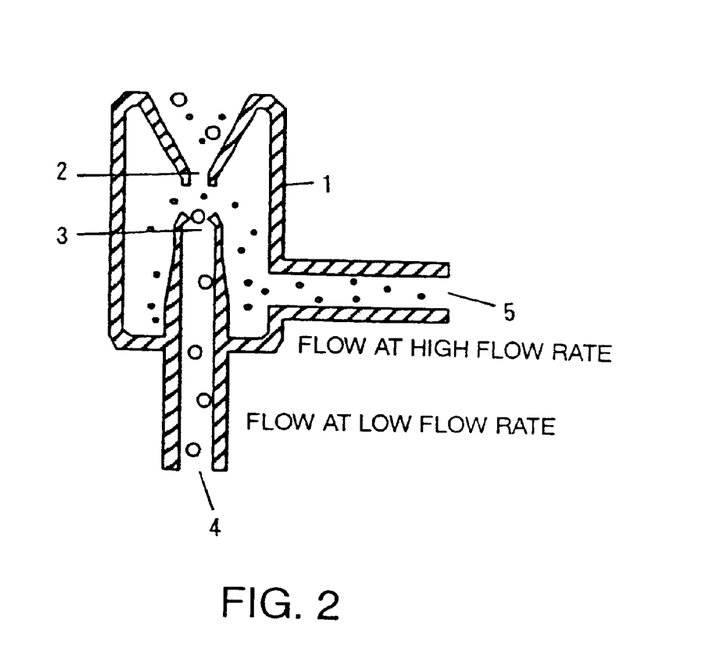
FIG. 2 is a schematic diagram showing an example of an impactor.

An example of a virtual impactor is shown in FIG. 2. This virtual impactor is composed of a receptacle 1 having a suction hole 2 and an extraction hole 3 placed in alignment with the suction hole 2. The receptacle 1 also has a first pump connection hole 4 which communicates with the extraction hole 2, and a second pump connection hole 5 which communicates with the receptacle 1. The flow rate of a suction flow through the second pump connection hole 5 is set higher than the flow rate of a suction flow through the first pump connection hole 4 (for example, the flow rate of a suction flow through the second pump connection hole 5 is 30 L/min, the flow rate of a suction flow through the first pump connection hole 4 is 2 L/min) to enable only larger particles to be introduced into the extraction hole 3 placed in alignment with the suction hole 2, whereby separating is performed according to the particle size.

In the method of the present invention, the virtual impactor is designed so as to be able to separate only particles of a particle size equal to or larger than a certain value (e.g., 6 $\mu$m) to remove particles substantially smaller than pollen grains. Such a design is well-known to those skilled in this field. It is known that the size of particles separated by the virtual impactor is determined by the number and the diameter of suction holes (jet nozzles) 2, the flow rate of the suction flow through the second pump connection hole 5, etc., and can be calculated by the following equation, for example.

$$dp_{50}=\sqrt{(18\psi_{50}N\pi 60Dc^3/4CQ\rho)}$$

dp: aerosol particle diameter (cm)

C: Cunningham's slip correction coefficient $$(1.0+0.16\times 10^4/dp^{-1})$$

Q: suction flow rate (1/min)

$\rho$: specific gravity of aerosol (g/cm$^3$)

$\mu$: viscosity of air (1.8×10$^{-4}$ g/cm/sec)

N: number of jet nozzles

Dc: diameter of jet nozzles (cm)

$\Psi_{50}$: nondimensional inertia parameter (=0.144)

Particles separated by a separating means such as the thus-designed virtual impactor are caused to flow through the flow cell in such a state that self-fluorescence from each of the particles can be measured. The flow rate of particles passing through the flow cell is controlled so that the particles are sufficiently spaced apart from each other when passing through the flow cell, thereby enabling self-fluorescence from each of the particles to be measured.

Ordinarily, the flow cell is connected between the first pump connection hole 4 and a pump connected to the first pump connection hole 4. In such an arrangement, one pump can function both as a pump for sucking in particles through the extraction hole 2 and as a pump for causing particles to flow through the flow cell.

Figure 3:
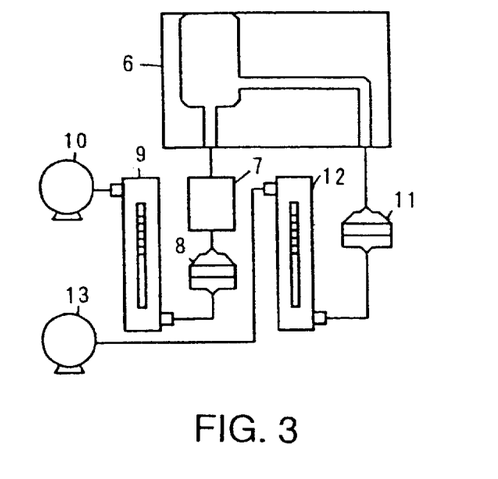
FIG. 3 is a schematic diagram showing an example of an impactor and a fluidizing means.

FIG. 3 shows an example of such an arrangement. A first pump 10 is connected to the first pump connection hole 4 through a flow cell in a measuring means 7, an air filter 8 and a flowmeter 9. A second pump 13 is connected to the second pump connection hole 5 through an air filter 11 and a flowmeter 12. The flow rate of the suction flow caused by the second pump 13 is set higher than the flow rate of the suction flow caused by the first pump 10, thereby enabling only larger particles to be introduced into the extraction hole 3 placed in alignment with the suction hole 2. Thus, separating according to the particle size is performed. The flow rate of the suction flow caused by the first pump 10 is controlled so that self-fluorescence from each of the particles can be measured.

It is possible to remove a substantially large part of diesel particles, burning-residue ash, bacteria, or the like, by separating particles other than those substantially smaller than pollen grains, e.g., particles of a particle size equal to or larger than 6 $\mu$m. However, particles having substantially the same size as that of pollen grains, e.g., those in a cloud of dust or the like are not distinguishable from pollen grains only by comparison of the particle sizes thereof. Therefore, pollen grains are discriminated based on self-fluorescence of particles. That is, it has been reported that while organic materials such as pollen and bacteria have self-fluorescence, inorganic materials such as those forming a cloud of dust do not have self-fluorescence. If particles passing through the flow cell are irradiated with excitation light (having a wavelength of, ordinarily, 300 to 500 nm), and self-fluorescence (ordinarily in a wavelength range from 440 to 650 nm) from the irradiated particles is observed, particles of organic materials such as pollen and particles of inorganic materials such as particles in a cloud of dust can be discriminated from each other.

The self-fluorescence can be measured by detecting light of fluorescence emitted from the particles passing through the flow cell with excitation light.

A laser for emitting light of one wavelength, a combination of an electric light and a bandpass filter, etc., can be used as a light source of excitation light. Excitation light may be emitted as a beam in the form of a sheet through a lens or the like. To detect fluorescence, a photomultiplier tube or the like may be used.

In the method of the present invention, it is preferable to measure scattered light as well as self-fluorescence from particles passing through the flow cell.

Figure 4:
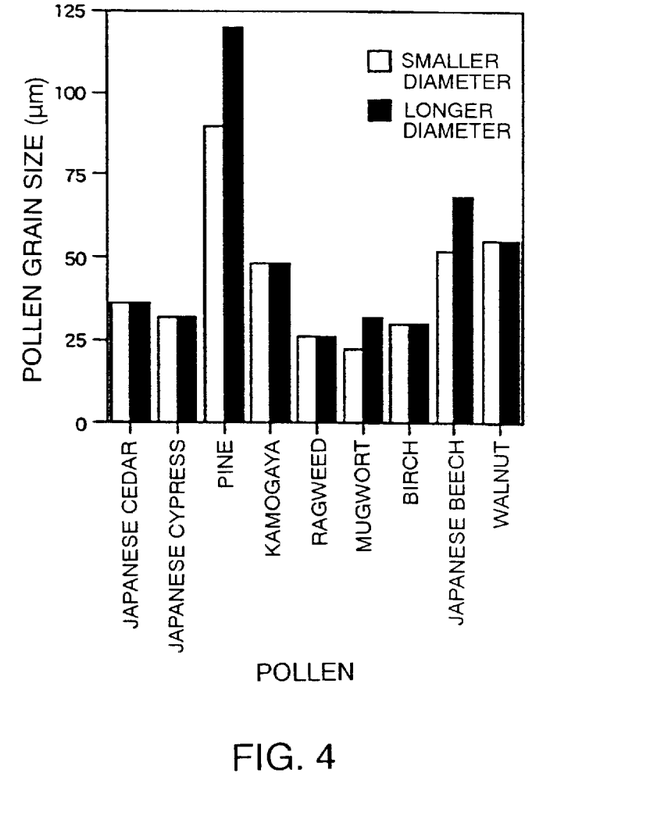
FIG. 4 is a diagram showing the diameter (smaller diameter and larger diameter) of various kinds of pollen.

Scattered light reflects the size of particles. It is possible a shape will be presumed to a certain degree, such as a spherical shape and a rod-like shape, from a combination of forward scattered light and side scattered light in particular. As shown in FIG. 4, different kinds of pollen have diameters (larger diameter and smaller diameter) specific to their kinds. Therefore, it is possible to obtain indices important in determination of the kind of pollen by presuming the size and shape of particles through measurement of scattered light.

Scattered light can be measured by detecting light scattered from particles passing through the flow cell. As scattered light, forward scattered light which is emitted forward in the direction of irradiation of excitation light and side scattered light which is emitted in a lateral direction with respect to the direction of irradiation of excitation light (ordinarily, at an angle of about 90°), are usually measured. As a light source of this irradiation light, the same light source as that for emitting excitation light can be used. To detect scattered light, a photomultiplier tube or the like may be used.

The wavelength of irradiation light for measurement of scattered light and that of excitation light for measurement of self-fluorescence may be the same to enable the use of common irradiation light for measurement of scattered light and measurement of self-fluorescence.

Different kinds of pollen vary in size and shape (FIG. 4), and also vary in self-fluorescence characteristics. From observation of self-fluorescence of various kinds of pollen, it can be understood that there are differences in color, for example, the pollen of Japanese cedar has substantially bluish green self-fluorescence, and the pollen of Japanese cypress has reddish yellow self-fluorescence. Therefore, it is preferable to analyze self-fluorescence by decomposing it into a blue component, a green component and a red component. Specific differences appear particularly strongly in the blue component (ordinarily, of a wavelength of 440 to 500 nm) and the red component (ordinarily, of a wavelength of 570 to 650 nm) of self-fluorescence. The ratio of the blue component and the red component is useful in discrimination of kinds of pollen, and it is, therefore, preferable to measure the blue and red components. For example, the color components of self-fluorescence can be measured by decomposing self-fluorescence by a combination of half mirrors and bandpass filters or a three primary colors decomposition prism.

Counting based on measured values can be performed by an information processor such as a computer.

Figure 5:
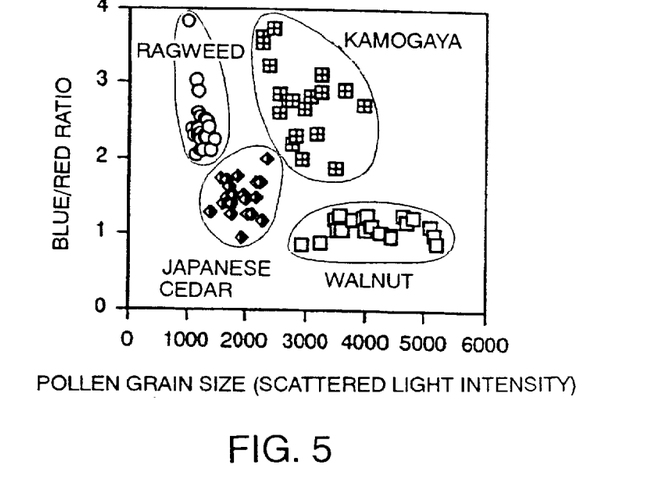
FIG. 5 is a diagram showing the results of discrimination of pollens according to scattered light and characteristics of self-fluorescence.

As described above, different kinds of pollen vary in size, shape and self-fluorescence characteristics. Therefore, it is possible to compute the kinds and the number of grains of pollen by counting the number of particles with respect to these indices and combinations of these indices. That is, the size and the flatness (the ratio of the long and short diameters) of pollen grains are computed on the basis of measured scattered light values, and self-fluorescence characteristics (the ratio of the blue component and the red component, etc.) are computed on the basis of measured values of the blue component and the red component of self-fluorescence. Discrimination and count are performed on the basis of the results of the computation. Indices used for discrimination can be selected as desired according to the characteristics of measurement object pollens. FIG. 5 shows an example of discriminations made in this manner. It can be understood from FIG. 5 that the pollens of ragweed, kamogaya (*Dactylis glomerata*), Japanese cedar, and walnut can be definitely discriminated from each other on the basis of the pollen size (the intensity of scattered light) and the ratio of the blue component and the red component (Blue/Red ratio) of self-fluorescence.

Further, even if a number of kinds of pollen are mixed, they can be discriminated from each other by measuring these indices with respect to the kinds of pollen and suitably selecting and combining the indices appropriately showing the differences between the kinds of pollen.

<2> Apparatus of the Present Invention

The apparatus of the present invention has a separating means of separating particles other than those substantially smaller than pollen grains, contained in a given amount of air, a fluidizing means of causing the separated particles to flow through a flow cell in such a state that self-fluorescence from each of the particles can be measured, a measuring means of measuring self-fluorescence from each of the particles passing through the flow cell, a counting means of counting the number of particles based on a measured value, and an outputting means of outputting a count result.

There is no particular restriction on the separating means as long as the separating means can remove particles substantially smaller than pollen grains to separate suitable particles. Preferably, the virtual impactor described above with respect to the method of the present invention is used as the separating means.

The fluidizing means causes the separated particles to flow through a flow cell in such a state that self-fluorescence from each of the particles can be measured. The fluidizing means can be constituted by a conduit connected to the flow cell, and a pump. The size of the flow cell and the flow rate in the flow cell are suitably selected to enable measurement of self-fluorescence from individual particles. As described above with respect to the method of the present invention, if a virtual impactor is employed, a pump for operating the virtual impactor can be provided as a common pump also used for the fluidizing means.

The measuring means can be constituted by a means of irradiating particles passing through the flow cell with excitation light, and a means of detecting fluorescence emitted from the particles.

As the excitation light-irradiating means, a laser for emitting light of one wavelength, a combination of an electric light and a bandpass filter, etc., can be used. Excitation light may be emitted as a beam in the form of a sheet through a lens or the like. To detect fluorescence, a photomultiplier tube, a CCD, or the like may be used.

Preferably, the measuring means comprises means of measuring scattered light. More preferably, the measuring means comprises a means of measuring forward scattered light and a means of measuring side scattered light.

Also, preferably, the measuring means comprises a means of measuring a blue component and a red component of self-fluorescence. This means may be constituted by, for example, a means of decomposing self-fluorescence to obtain a blue component and a red component, such as a combination of half mirrors and bandpass filters or a three primary colors decomposition prism, and a means of detecting each color component, such as a photomultiplier tube or a CCD.

There is no particular restriction on the counting means as long as the counting means is capable of counting the number of pollen grains based on a measured value. For example, the counting means may comprise an information processor such as a computer having an A/D converter.

The outputting means may comprise a display (a CRT monitor or the like), a printer, a communication unit, etc.

Figure 6:
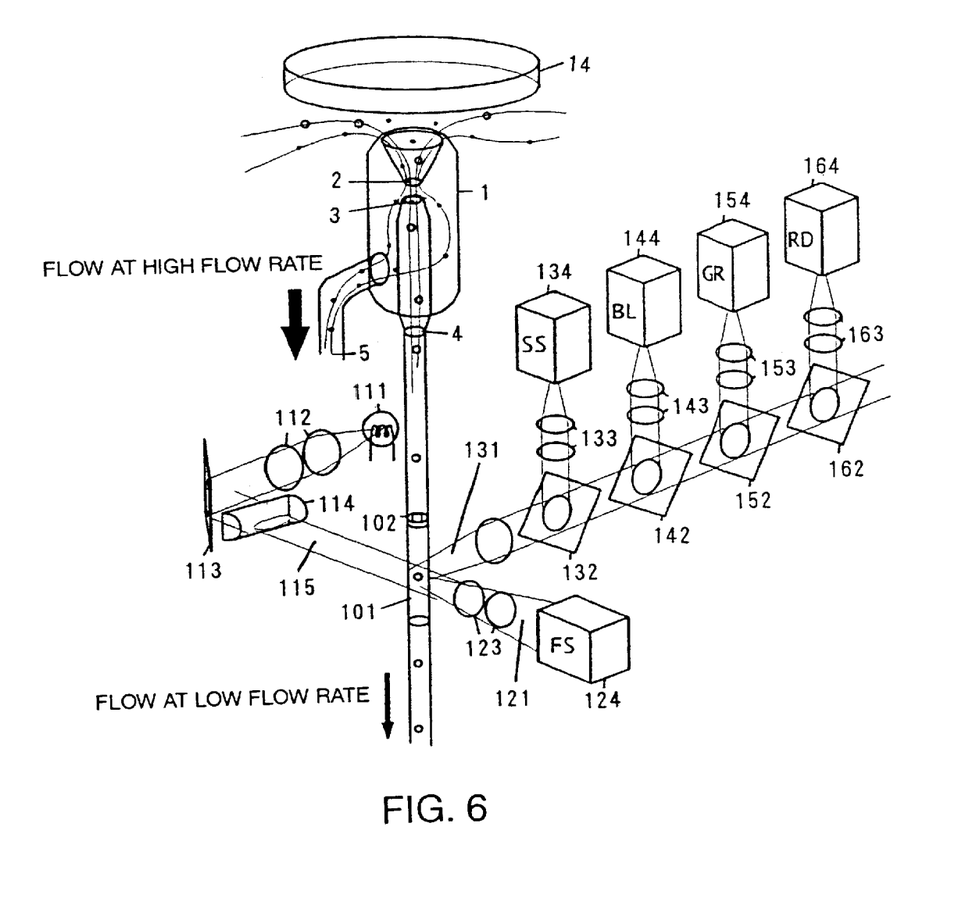
FIG. 6 is a schematic diagram showing an example of an arrangement of a separating means, a fluidizing means and a measuring means.

An example of an arrangement of the separating means, the fluidizing means and the measuring means of the apparatus of the present invention will now be described with reference to FIG. 6.

The separating means and the fluidizing means are composed of a virtual impactor, and a flow cell 101 and a pump (not shown) connected to the virtual impactor. A first pump is connected through the flow cell 101 to a first pump connection hole 4 which communicates with an extraction hole 3. A second pump is connected to a second pump connection hole 5 which communicates with a receptacle 1 of the virtual impactor. A hood 14 is provided above a suction hole 2. An air filter 102 for regulating a flow is provided immediately upstream of the flow cell 101.

The measuring means has, as a means of irradiation with excitation light 115 in an ultraviolet region, a light source 111, an excitation light bandpass filter 112 for selecting, from light from the light source 111, a wavelength suitable for excitation light 115, a reflecting mirror 113, and a lens 114 for suitably shaping the beam of excitation light 115.

The measuring means also has, as a means of measuring forward scattered light 121, a forward scattered light bandpass filter 123 which is placed in the direction of irradiation of excitation light and which selects light of a wavelength corresponding to scattered light, and a forward scattered light-detecting photomultiplier tube 124 for detecting light passing through the forward scattered light bandpass filter 123.

Figure 7:
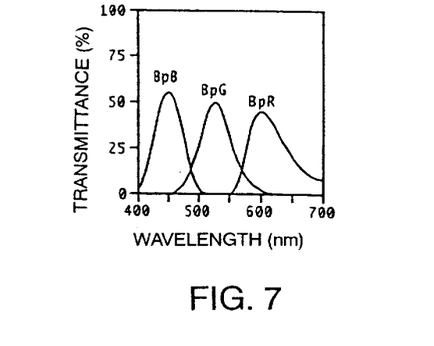
FIG. 7 is a diagram showing an example of the transmittance of a bandpass filter.

Further, the measuring means has, as means of measuring side scattered light and fluorescence 131, a side scattered light-reflecting half mirror 132 which is placed in a direction at an angle of 90° from the direction of irradiation of excitation light, and which reflects light of a wavelength corresponding to side scattered light and allows light of a wavelength corresponding to fluorescence to pass therethrough, a side scattered light bandpass filter 133 for selecting light of the wavelength corresponding to scattered light from the light reflected by the side scattered light-reflecting half mirror 132, a side scattered light-detecting photomultiplier tube 134 for detecting light passing through the side scattered light bandpass filter 133, a blue light-reflecting half mirror 142 which reflects light of the blue component of fluorescence and allows light of the green component and the red component of fluorescence to pass therethrough, a blue light bandpass filter 143 for selecting light of the blue component of fluorescence from the light reflected by the blue light reflecting half mirror, a blue light-detecting photomultiplier tube 144 for detecting light passing through the blue light bandpass filter 143, a green light-reflecting half mirror 152 which reflects light of the green component of fluorescence and allows light of the red component of fluorescence to pass therethrough, a green light bandpass filter 153 for selecting light of the green component of fluorescence from the light reflected by the green light-reflecting half mirror, a green light-detecting photomultiplier tube 154 for detecting light passing through the green light bandpass filter 153, a red light-reflecting half mirror 162 which reflects light of the red component of flurorescence, a red light bandpass filter 163 for selecting light of the red component of fluorescence from the light reflected by the red light-reflecting half mirror, a red light-detecting photomultiplier tube 164 for detecting light passing through the red light bandpass filter 163, a collective lens 135 for suitably shaping the beam of side scattered light and the beam of fluorescence 131 emitted from the flow cell 101. FIG. 7 shows transmittance characteristics of the blue light bandpass filter 143, the green light bandpass filter 153 and the red light bandpass filter 163.

Figure 8:
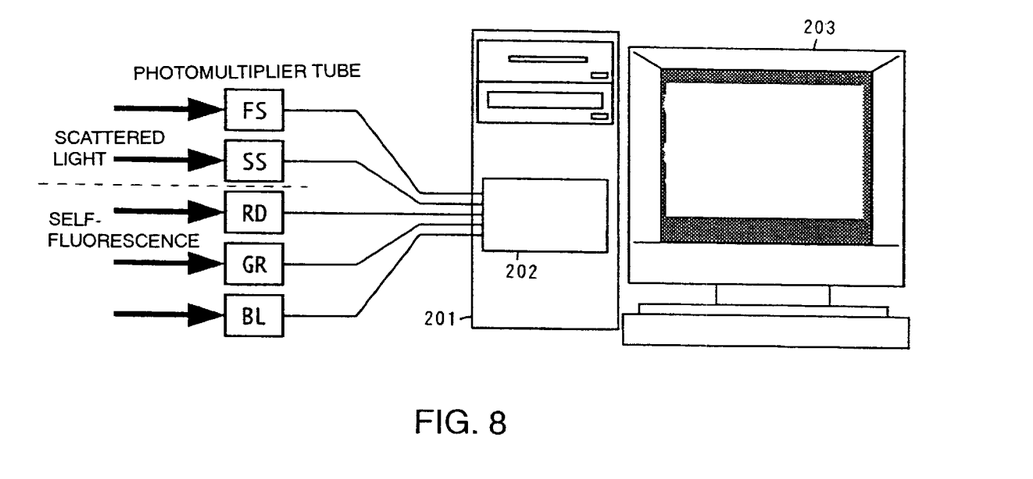
FIG. 8 is a schematic diagram showing an example of an arrangement of a counting means and an outputting means in the apparatus of the present invention.

An example of an arrangement of the counting means and the outputting means used in the present invention will be described next with reference to FIG. 8.

The counting means is composed of a computer 201 having an A/D converter 202 connected to the respective photomultiplier tubes. Software for counting on the basis of data input from the A/D converter 202 is installed in the computer 201.

The outputting means is composed of a display 203.

In operation of this example of the apparatus, the first pump and the second pump are operated so that particles other than those substantially smaller than pollen grains are separated by the virtual impactor. The separated particles are caused to flow through the flow cell 101 in such a state that scattered light and fluorescence from each of the particles can be measured.

The flow cell 101 is irradiated with excitation light 115 by the means of irradiation with excitation light 115, and forward scattered light, side scattered light, and the blue component, the green component and the red component of fluorescence are detected by the forward scattered light-detecting photomultiplier tube 124, the side scattered light-detecting photomultiplier tube 134, the blue light-detecting photomultiplier tube 144, the green light-detecting photomultiplier tube 154, and the red light-detecting photomultiplier tube 164, respectively.

Outputs from the respective photomultiplier tubes are put into the computer 201 through the A/D converter 202. The software installed in the computer 201 counts signals representing fluorescence, computes the number of pollen grains in a given amount of atmosphere from the sucked volume computed from the suction flow rate in the virtual impactor, and counts with respect to each kind of pollen from signals of the respective components of scattered light and fluorescence on the basis of the predetermined relationship among the respective components of scattered light and fluorescence.

The results of counting are displayed on the display 203.

Industrial Applicability

With the use of the present invention, as described above, separation of particles according to the size and discrimination based on self-fluorescence are combined to enable only pollen existing in a given amount of atmosphere to be automatically quantified. Also, counting of particles is performed according to the size, shape and fluorescence characteristics of particles having self-fluorescence or to a combination of these, thus enabling measurement of the kind and number of pollen grains.

What is claimed is:

1. A pollen grain-counting method comprising separating particles contained in a given amount of atmosphere by removing the particles that are substantially smaller than pollen grains from the particle flowing through a flow cell in such a state that self-fluorescence from each of the separated particles can be measured, measuring a ration of a blue component and a read component of self-fluorescence from each of the particles passing through the flow cell, and counting the number of particles based on a measured value comprising the ratio.

2. A counting method according to claim 1, wherein separation is performed by a virtual impactor.

3. A counting method according to claim 1 or 2, wherein scattered light is measured together with the ratio of the blue component and the red component of the self-fluorescence.

4. A counting method according to claim 3, wherein the scattered light to be measured includes forward scattered light and side scattered light.

5. A counting method according to claim 1, wherein the counting step comprises discriminating kinds of pollen based on the measured value comprising the ratio.

6. A pollen grain-counting apparatus comprising a separating means of separating particles contained in a given amount of atmosphere by removing the particles that are substantially smaller than pollen grains from the particle flowing, a fluidizing means of causing the separated particles to flow through a flow cell in such a state that self-fluorescence from each of the separated particles can be measured, a measuring means of measuring a ration of a blue component and a read component of self-fluorescence from each of the particles passing through the flow cell, and a counting means of counting the number of particles based on a measured value comprising the ratio, and an outputting means of outputting a count result.

7. A counting apparatus according to claim 6, wherein the separating means is a virtual impactor.

8. A counting apparatus according to claim 6, wherein the measuring means further comprises a means of measuring scattered light.

9. A counting apparatus according to claim 8, wherein the measuring means further comprises a means of measuring forward scattered light, and a means of measuring side scattered light.

10. A counting apparatus according to claim 6, wherein the counting means comprises a discriminating means of discriminating kinds of pollen based on the measured value comprising the ratio.

* * * * *

UNITED STATES PATENT AND TRADEMARK OFFICE
CERTIFICATE OF CORRECTION

| | |
|---|---|
| PATENT NO. | : 6,594,001 B1 |
| DATED | : July 15, 2003 |
| INVENTOR(S) | : Yabusaki |

It is certified that error appears in the above-identified patent and that said Letters Patent is hereby corrected as shown below:

Column 8,
Lines 24 and 47, "ration" should read as -- ratio --.
Line 48, "read" should read as -- red --.

Signed and Sealed this

Twenty-fifth Day of November, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,594,001 B1
DATED : July 15, 2003
INVENTOR(S) : Yabusaki

It is certified that error appears in the above-identified patent and that said Letters Patent is hereby corrected as shown below:

Column 8,
Line 25, "read" should be -- red --.

Signed and Sealed this

Twenty-seventh Day of January, 2004

JON W. DUDAS
*Acting Director of the United States Patent and Trademark Office*